United States Patent [19]

Wassiliew, deceased et al.

[11] Plant 4,780

[45] Oct. 20, 1981

[54] DWARF PEACH W-114

[75] Inventors: Fedor Wassiliew, deceased, late of Orange, Calif.; by Nicolaus Wassiliew, heir, Costa Mesa, Calif.; by Alexander Wassiliew, heir; by Marsha W. Hartman, heir, both of Orange, Calif.; by Valentina Wassiliew, heir, Costa Mesa, Calif.

[73] Assignee: Jackson & Perkins Co., Medford, Oreg.

[21] Appl. No.: 145,510

[22] Filed: May 1, 1980

[51] Int. Cl.[3] ..... A01H 5/00

[52] U.S. Cl. ..... Plt./43

[58] Field of Search ..... Plt./43

*Primary Examiner*—James R. Feyrer

*Attorney, Agent, or Firm*—Klarquist, Sparkman, Campbell, Leigh, Whinston & Dellett

[57] ABSTRACT

A new dwarf peach plant has semi-double pink flowers with late July ripening fruit. The fruit is nearly spherical with a red flushed yellow skin, its flesh being sweet and yellow.

3 Drawing Figures

This present invention relates to a new and distinct variety of peach tree of the genetically dwarf type, having pink flowers and freestone, yellow fleshed fruit. The original seedling of this new peach was discovered by Fedor Wassiliew among seedlings grown from various crosses made by Mr. Wassiliew in Orange, California. The exact parentage is unknown.

The primary objective of the breeding program was to produce a variety of.dwarf peach, usable as an ornamental plant in home gardens and producing an edible, tasteful fruit of good texture and juice content. This objective was fully achieved along with other desirable features, as evidenced by the following unique combination of characteristics which are outstanding in the new variety and which distinguish it from all other varieties:

1. A vigorous plant of dwarf character, attaining less than three feet height in four growing seasons.
2. An abundance of semi-double pink flowers.
3. Ripening date at Irvine, Calif. approximately July 20th.
4. Round, red flushed yellow fruit with shallow suture.
5. Heavy fruit set at Irvine, Calif.
6. Firm, yellow flesh, darker in color than the flesh of Bonanza, U.S. Plant Pat. No. 2,213.

Asexual reproduction of this new peach variety as performed by budding at Wasco, Calif. shows that the foregoing characteristics are established and come true to form through succeeding propagations.

The accompanying illustrations show typical specimens of the plant, leaves, flowers, fruit and seed of this new variety depicted in color as nearly true as it is reasonably possible to make the same in a color illustration of this character.

The following is a detailed description of this new variety, as based upon observations of specimens grown at Irvine, Calif., with color terminology in accordance with the Royal Horticultural Colour Chart, except where general color terms of ordinary dictionary significance are obvious.

PLANT

Habit: Genetically dwarf; internodes less than ¼ inch long; reaching less than 3 feet in height in four years; spreading; often broader than tall.

Chilling requirement: About equal to that of the variety Bonanza, U.S. Plant Pat. No. 2,213, bearing abundant fruit at Irvine, Calif.

Leaves:

*Size.*—Length: approximately 6 to 7 inches; pendulous.

*Color.*—Upper surface: near RHS 131A. Under surface: RHS 131D.

FLOWERS

Blooming habit: Flowers are borne heavily the same time as Bonanza to four or five days later.

Size: Approximately 1¼ inches diameter.

Petalage: 6 to 8 petals.

Color (open flower): Mostly near RHS 62C, except basal quarter of petal which is near RHS 57D.

FRUIT

Ripening date: Near July 20th at Irvine, Calif.

Size: After having been thinned, 2½ to 3 inches in diameter; nearly spherical; slightly wider on suture plane.

Suture: Very shallow.

Skin:

*Color.*—Near RHS 29B with numerous flecks of red becoming streaks of red near the stem end.

*Pubescence.*—From moderate to light.

Flesh:

*Quality.*—Juicy texture; melting, but firm when ripe.

*Aroma.*—Pronounced.

*Flavor.*—Sweet, low acid.

*Color.*—Near RHS 22B except streaked heavily in the pit cavity with red near RHS 42A and RHS 42B.

Stone:

*Tenacity of flesh.*—Stone not attached to flesh.

*Color.*—Near RHS 187B.

I claim:

1. A new and distinct variety of peach tree of the genetically dwarf type, substantially as herein shown and described, characterized particularly as to novelty by its unique combination of vigorous, dwarf plant, semi-double pink flowers, late July ripening date, nearly spherical, red flushed yellow fruit skin, and sweet yellow flesh.

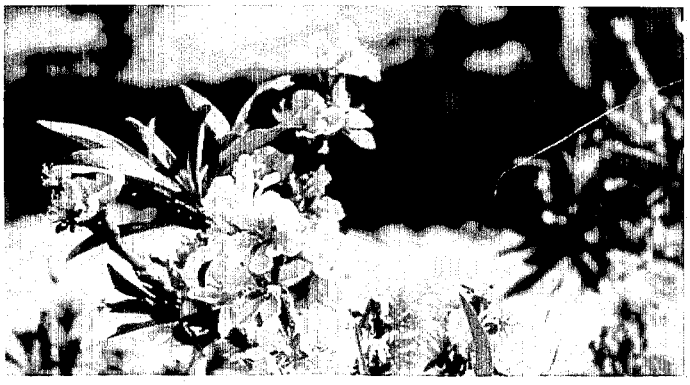
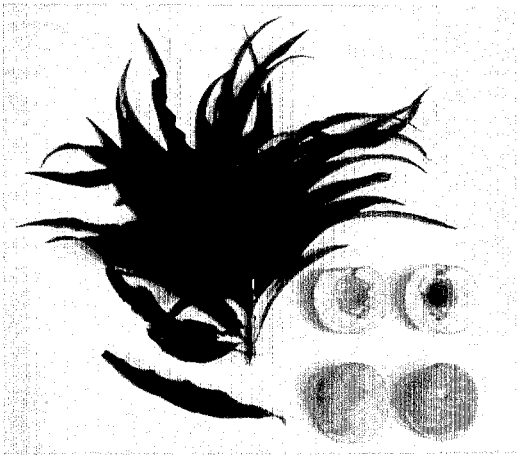
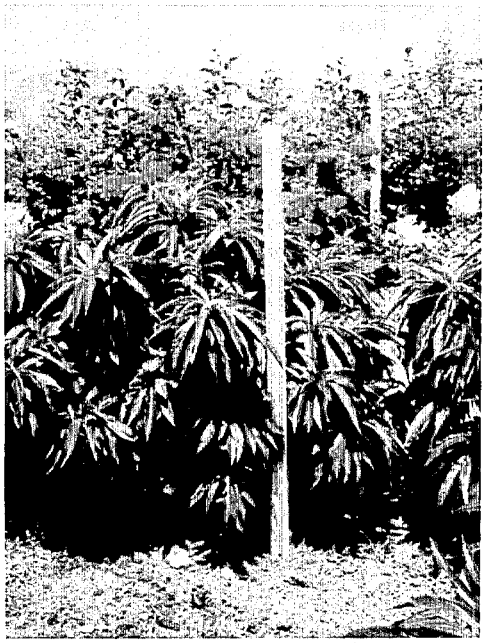

* * * * *